United States Patent [19]

Wassmundt

[11] Patent Number: 5,679,695
[45] Date of Patent: Oct. 21, 1997

[54] ARYL AND HETEROARYL COMPOUNDS HAVING ANTI-RETROVIRUS ACTIVITY

[75] Inventor: Frederick William Wassmundt, Willimantic, Conn.

[73] Assignee: The University of Connecticut, Storrs, Conn.

[21] Appl. No.: 378,921

[22] Filed: Jan. 25, 1995

Related U.S. Application Data

[63] Continuation of Ser. No. 715,519, Jun. 14, 1991, abandoned, which is a continuation-in-part of Ser. No. 601,336, Oct. 22, 1990, abandoned.

[51] Int. Cl.$^6$ .............................. A61K 31/44; A61K 31/10
[52] U.S. Cl. .............................. 514/347; 514/706; 514/708; 514/709; 514/712
[58] Field of Search ...................... 568/29, 30; 514/708, 514/709, 347, 706, 712; 546/294

[56] References Cited

U.S. PATENT DOCUMENTS

| | | | |
|---|---|---|---|
| 3,661,944 | 5/1972 | Dowalo et al. | 564/300 |
| 4,038,412 | 7/1977 | Grisar et al. | 424/330 |
| 4,349,567 | 9/1982 | Markley et al. | 424/330 |
| 4,349,568 | 9/1982 | Markley et al. | 424/330 |
| 4,371,537 | 2/1983 | Markley et al. | 424/263 |
| 4,616,087 | 10/1986 | Wood | 546/294 |
| 4,692,466 | 9/1987 | Yoshimoto et al. | 514/604 |
| 4,831,194 | 5/1989 | Kreidl et al. | 514/708 |
| 4,889,863 | 12/1989 | Dolman et al. | 514/312 |
| 4,973,599 | 11/1990 | Gilman et al. | 514/398 |
| 4,978,687 | 12/1990 | Pascuchi | 514/708 |
| 4,992,430 | 2/1991 | Seydel et al. | 514/155 |
| 5,026,895 | 6/1991 | Bakos et al. | 560/21 |
| 5,075,326 | 12/1991 | Beck et al. | 514/369 |

FOREIGN PATENT DOCUMENTS

| | | |
|---|---|---|
| 102476 | 3/1984 | European Pat. Off. . |
| 0181526 | 5/1986 | European Pat. Off. . |
| 0256486 | 2/1988 | European Pat. Off. . |
| 4936828 | 4/1974 | Japan .................. 514/707 |
| 00055 | 1/1990 | WIPO . |
| 9000055 | 1/1990 | WIPO . |
| 01124 | 2/1991 | WIPO . |
| 9101124 | 2/1991 | WIPO . |

OTHER PUBLICATIONS

McMahon et al., Antimicrobial agents and Chemotherapy, vol. 37, No. 4, pp. 754–760 1993.

Weise et al., Quant. Struct. Act. Relat., vol. 6, No. 4, pp. 164–172 1987.

Popoff et al., J. Med. Chem, vol. 14, No. 12, pp. 1166–1169 1971.

Winklemann et al., Arzneim. Forsch., vol. 26, No. 8, pp. 1543–1547 1976.

Pappalardo et al., Conformational Properties . . . , vol. 33, No. 12, pp. 945–953 1978.

STN file supplier, RN =127–63–9, 26–27 1220–92–4, 18739–95–2 1967.

Mohan, et al., Inhibition of HIV Replication by Naphtralenemonosulfonic Acid Derivatives and a Bis Naphthalenedisulfonic Acid Compound Life Sciences, vol. 47, pp. 993–999 1990.

Hansch, et al., A survey of Hammett Substituent Constants and Resonance and Field Parameters, Chem. Rev. 1991, 165–195.

Markley, et al., Antipicornavirus Activity of Substituted Phenoxybenzenes and Phenoxypyridines, J. Med. Chem., 1986, 29, 427–433.

Chemical Abstracts 1968, 69, 1890m.

Chemical Abstracts 1933, 27, 998.

David, et al., Effects of Antituberculosis and Antileprosy Drugs on Mycobacteriophage D29 Growth, Antimicrobial Agents and Chemotherapy, Aug. 1980, pp. 357–359.

McMahon et al, Antimicrobial agents and chemotherapy, vol. 37, No. 4, 754–760, 1993.

Pappalardo et al, IL Farmaco, Ed. Sc. vol. 33, 945–953, 1978.

Winkelmann et al, Argneim —Forsch. 26, No. 8, 1976.

Popoff et al, J. Med. Chem., 1971, vol. 14, No. 12, 1166–1169.

Wiese et al, Quant Struct–Act. Relat., 6, 164–172, 1987.

*Primary Examiner*—Shailendra Kumar
*Attorney, Agent, or Firm*—Hamilton, Brook, Smith & Reynolds, P.C.

[57] ABSTRACT

The present invention relates to a method of treating a retrovirus utilizing a compound of the formula

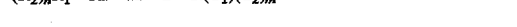

$(R_2)_n R_1—Ar—X—Y—R(T_1)(T_2)_m$      I The present invention also relates to pharmaceutical compositions in which the active ingredient has a compound of formula I.

6 Claims, 2 Drawing Sheets

ARYL AND HETEROARYL COMPOUNDS HAVING ANTI-RETROVIRUS ACTIVITY

RELATED APPLICATION

This application is a continuation of Ser. No. 07/715,519, filed Jun. 14, 1991, now abandoned, which is a continuation-in-part of U.S. application having Ser. No. 601,336, which was filed on Oct. 22, 1990, now abandoned.

FIELD OF THE INVENTION

The present invention relates to heteroaryl or aryl containing compounds useful for treating or arresting the progression of a retroviral infection in an animal. Furthermore, the present invention is directed to a method of treating a disease attributable to a retrovirus infection which comprises administering to the animal a therapeutically effective amount of an aryl or heteroaryl containing compound. The present invention is also directed to a pharmaceutical composition containing these compounds.

Background of the Invention

Retroviruses contain a (+) RNA genome inside an icosahedral shell. This spherical nucleoprotein core is surrounded by an envelope which consists of a viral encoded glycoprotein molecule in a liquid bilayer which is derived from the plasma membrane of the host.

The retrovirus infects a host cell by binding to specific receptors on the surface from which it can enter the cell. The viral (+) RNA is uncoated in the cytosol. Reverse transcriptase brought in by the virus particle syntheses both (−) and (+) DNA. The DNA genome so synthesized enters the nucleus and becomes integrated in the host cell. Genomic RNA is formed from the transcription of the DNA, and the RNA is translated to form viral protein. The genome RNA and viral proteins migrate to the plasma membrane and become incorporated into it. A portion of the altered membrane builds to form a new retrovirus. The DNA generated from the retrovirus remains in the genome of the infected cell continuing to be expressed. It is even replicated, along with the host DNA. The replicated DNA is then passed on to the daughter cells. Thus, unlike most viral infections, the retrovirus does not rupture or cause the rupturing of a host cell.

Retrovirus infections are implicated in a number of diseases, including the Acquired Immune Deficiency Syndrome (AIDS) and the elated disease AIDS related complex (ARC). AIDS and ARC are believed to result from infection by the human immunodeficiency virus (HIV) and antibodies to which are found in the serum of almost all people diagnosed as suffering from AIDS or ARC. Lymphadnopathy-associated virus (LAV) and human T-lymphotrophic virus type III (HTLV-III) as well as related retroviruses have been isolated form a a large number of AIDS patients. All of these viruses share important characteristics. HTLV-III and LAV are now believed to be strains of the same virus, which has been given the name Human Immunodeficiency Virus (HIV).

AIDS is a disease characterized by loss of cell-mediated immunity and the development of frequent and eventually fatal opportunistic infections. The diagnosis of AIDS is a clinical one, defined as "the occurrence of an illness predictive of a defect in cell-mediated immunity occurring in an individual with no known cause for diminished resistance of that disease" (Lane, H. C. & Fauci, A. S. Ann. Rev. Immunol. 1985, 3, 477–500).

The use of the term HIV embraces the retrovirus HIV-1 or HIV-2 (Human Immunodeficiency Virus Type 1 and Human Immunodeficiency Virus Type 2), which was discovered in 1983. HIV attacks and reduces the numbers of a subset of white blood cells known as T lymphocytes. Expressed on the cell surfaces of these T lymphocytes is a molecule known as CD4, (such cells are also known as T4 cells). Such lymphocytes, most of which are included in what is functionally defined as the helper/inducer subset, constitute the major proportion of mature T cells. Another major subset of T cells express the CD8 molecule on their cell surfaces (such cells are also known as T8 cells). Most of these are classified as suppressor/cytotoxic cells. Normally the T4/T8 ratio is 1.5 to 2.0. In AIDS patients, however, this ratio is inverted due to a decrease in the absolute numbers of T4 cells, with normal numbers of T8 cells usually being preserved.

T4 cells specifically recognize and proliferate in response to antigens that they encounter in the body, at the same time releasing a variety of proteins known as lymphokines that regulate other immune system cells. Upon signaling by T4 cells, B lymphocyte cells recognize antigens and secrete specific antibodies to neutralize or eliminate antigenic bacteria and viruses as they travel through body fluids between cells. Similarly, following signaling from T4 cells, cytotoxic T cells ("T8") become activated to kill cells infected with intracellular pathogens. Furthermore, T4 cells modulate the activities of immune system cells known as natural killer cells and macrophages, which are involved in response to infection and perhaps to incipient malignancies.

A critical and early event in HIV infection involves the virus' attachment, via its envelope glycoprotein, to a receptor on the surface of a susceptible T4 cell, the CD4 molecule. The CD4 molecule at the T4 cell surface appears to distinguish potential target cells from HIV and to act as the receptor molecule that binds the virus and allows infection and subsequent viral replication as well as the cytopathic consequences of viral infection.

The immunodeficiency of AIDS clearly demonstrates the importance of T4 lymphocytes. Because of the loss of thee cells, the remaining T lymphocytes from AIDS patients have diminished or no responses to antigens and show subnormal production of essential immuno-regulatory factors. Because of their decreased numbers and functional capacity, T4 cells are unable to fulfill their necessary role in providing direction for the maturation of B cells and cytotoxic T cells. The ability of AIDS patients to mount antibody reactions to new antigens is severely compromised, though paradoxically high levels of antibodies to previously encountered antigens, including HIV, are often present in patients' sera.

At present AIDS and ARC are predominantly found in certain high risk groups such as homosexuals, intravenous drug abusers and those who have received multiple transfusions or products such as Factor VIII derived from blood. Blood donors are now routinely screened for antibodies to HIV and, therefore, future spread of HIV though blood transfusions and blood-derived products should not, hopefully, lead to transmission of AIDS. AIDS is also increasingly found in the heterosexual population.

There is increasing evidence that macrophage/monocyte infection is a vital factor in the persistence and progression of HIV infection, in initiating the brain damage that occurs in AIDS and in triggering the collapse of the immune system as evidenced by eventual profound depletion of T4 lymphocytes. Crowe et al. have demonstrated using anti-HIV p24 antibody that monocyte/macrophages can be infected with HIV. They have demonstrated that up to 70% of cells from individual donors could be infected (AIDS Research and Human Retroviruses, Vol. 3, No. 2, 1987, page 135). Nicholson et al. have proposed an HTLV-III/LAV-induced effect in monocyte function rather than (or in addition to) an intrinsic defect in surviving T cells to account for observed abnormalities in T cell assays that are monocyte-dependent such as pokeweed mitogen-induced Ig synthesis and proliferative responses to soluble antigens. These T cell assays have previously been reported as abnormal even when assayed as T cell subsets (The Journal of Immunology, Vol. 137, No. 1, 1986, page 323).

Since it is well established that the first event that occurs when a foreign material (for example, a virus) enters the body is its uptake by mononuclear phagocytes, it is conceivable that these cells represent a primary target for HIV. Gartner et al. have shown that virus production by THLV-III/LAV infected macrophages was high and long-lived, indicating that these cells may play a role in virus dissemination and persistence. They have demonstrated HTLV-III/LAV replication in macrophages was fully productive in the situations they evaluated (Science Vol. 233, 1986, page 215).

Salahuddin et al. observed that in vitro pulmonary macrophages can be injected with HTLV-III and appear to be less susceptible to the phytopathic effects of this retrovirus which suggests that tissue macrophages should be considered as potential reservoirs of HTLV-III in vivo (Blood, Vol. 68, No. 1, 1986, page 281).

Ho. D. D. et al. observed normal blood-derived monocytes/macrophages were found to be susceptible to infection in vitro by human T Lymphotropic virus III (HTLV-III), the etiologic agent of the Acquired Immune Deficiency Syndrome. In addition, HTLV-III was recovered from monocytes/macrophages of patients infected with this virus. It was postulated therefore that HTLV-III infected monocyte/macrophages may serve as a vehicle for the dissemination of virus to target organs and as a reservoir for viral persistence, as has been shown for other lentiviruses, including visna virus and caprine arthritis encephalitis virus (J. Clin. Invest, Vol. 77, 1986, page 1712).

While an antiviral agent which could kill all infecting HIV or completely inhibit its replication (and at the same time have an acceptable toxicity profile) is clearly desirable, the situation heretofore is that no such agent is at present available.

With the emerging understanding of the role that macrophages may be playing in the pathogenesis of AIDS, it is clear that an effective antiviral strategy will require an approach that can treat infected macrophages and inhibit infection of these cells. Currently the only F.D.A. approved antiviral agents for treatment of AIDS are azido thymidine (AZT) and pentamidine isethionate (PENTAM 300). However, the great majority of these antiviral agents are nucleosides or steroids. But AZT is not completely satisfactory. It does not appear to be completely effective at inhibiting macrophage infection or modulating HIV production from infected macrophages. Administration of AZT over long periods of time has been found to give rise to undesirable side effects such as anaemia, necessitating blood transfusion, leucopenia and neutropenia.

However, unlike the majority of the antiviral compounds, the compounds of the present invention are not nucleosides or steroids. The compounds of the present invention are much simpler molecules containing a bridging unit to an aryl or heteroaryl moiety, as described hereinbelow. However, despite their simplicity, the compounds of the present invention are effective in inhibiting retroviruses and particularly the HIV virus.

SUMMARY OF THE INVENTION

Figure 1:
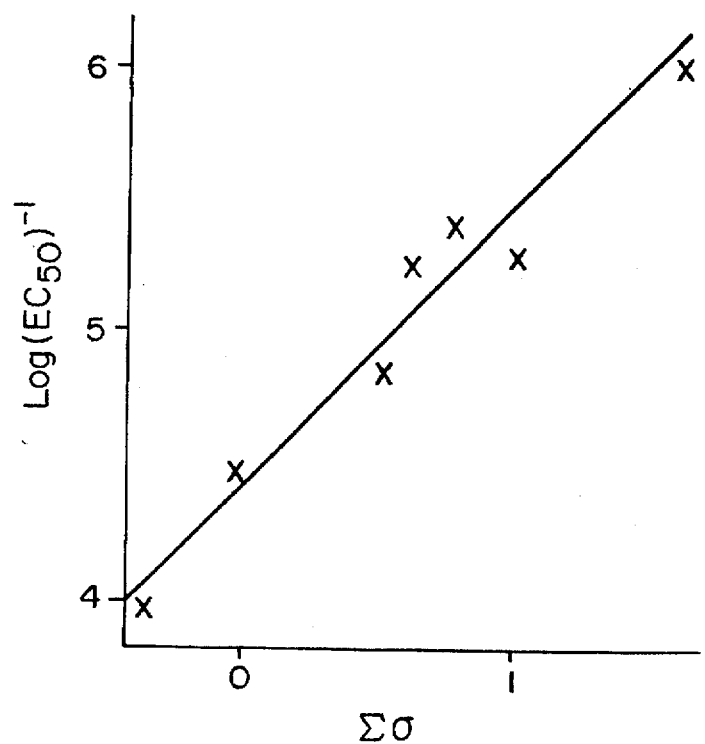
FIG. 1 is a plot of log $(EC_{50})^{-1}$ and $\sigma$ for diaryl sulfones.

The present invention encompasses compounds of the Formula I:

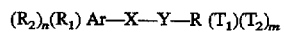

or pharmaceutically acceptable salts thereof, wherein

X is S, O, NH, SO, $SO_2$, $SO_2O$, $SO_2NG$,

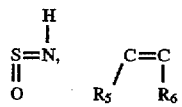

$SeO_2$, Se, or SeO,

Y is a chemical bond or $(CR_3R_4)_p$;

$R_3$ and $R_4$ are independently hydrogen or lower alkyl;

$R_5$ and $R_6$ are independently hydrogen or an electron withdrawing group;

G is hydrogen or lower alkyl, aryl, aryl lower alkyl, heterocyclic or heterocyclic lower alkyl;

R is an aryl group, lower aryl alkyl, lower alkyl, lower cycloalkyl, lower cycloalkyl lower alkyl, heterocyclic or heterocyclic lower alkyl;

$T_1$ and $T_2$ are independently hydrogen, electron donating or electron withdrawing group;

$R_1$ is an electron withdrawing group;

$R_2$ is hydrogen or lower alkyl;

Ar is aryl or heteroaryl;

n and m are independently 0–4; and p is 1–2.

The present invention is also directed to pharmaceutical compositions containing the compounds of the present invention in association with a pharmaceutical carrier. Furthermore, the present invention is directed to a method of treating retroviral infections, e.g., AIDS, in an animal in need of such treatment by administering to the animal an effective amount of a compound of Formula I.

DETAILED DESCRIPTION OF THE PRESENT INVENTION

The compound used in the present invention have the formula

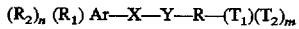

wherein $R_2$, $R_1$, Ar, Z, X, Y, R, $T_1$, $T_2$, n and m are defined hereinabove. In other words, a X=Y group bridges the Ar and R moieties.

Ar is an aryl or heteroaryl group.

As used herein, when used alone or in combination an "aryl" group is an aromatic group containing from 6 to 14 ring carbon atoms and up to a total of 18 carbon atoms. The aromatic group is planar. It may be monocyclic, bicyclic or polycylic. If it contains more than 1 ring, the aromatic group is a fused ring system. It includes such groups as phenyl, naphthyl, phenanthryl, anthryl and the like. The preferred aryl group is phenyl.

The term "heteroaryl", when used alone or in combination, is a nitrogen, sulfur or oxygen containing heteroaromatic group. The ring heteroatoms are either nitrogen, sulfur or oxygen. The heteroaryl groups may be monocyclic, bicyclic, or polycyclic; but if it contains more than 1 ring, the rings are fused. Furthermore, the heteroaryl groups are planar. The heteroaryl groups contain 1–4 ring heteroatoms and from 5–14 ring atoms. The heteroaryl group contains from 1–13 and preferably 3–13 ring carbon atoms and up to a total of 18 carbon atoms. The heteroaryl includes such groups as thienyl, benzothienyl, naphthothienyl, thianthrenyl, furyl, benzofuryl, pyrrolyl, imidazolyl, pyrazolyl, pyrridyl, pyrazinyl, pyrimidinyl, pyridazinyl, indolyl, indazolyl, purinyl, quinolyl, isoquinolyl, thiazolyl, isothiazolyl, oxazolyl, isooxazolyl, benzoxazolyl; benzoxathiazolyl, benzothiazolyl and benzoisothiazolyl, and the like, and the N-oxides of the nitrogen containing heteroaryl, such as the N-oxides of pyridyl, pyrazinyl, pyrimidinyl and the like. The preferred heteroaryl groups contain up to 10 ring atoms and 1 or 2 ring heteroatoms and up to a total of 15 carbon atoms. Preferably, the heterocyclic group contains at least 1 ring nitrogen atom. Preferred heteroaryl groups include pyridyl, pyrimidinyl, pyrazinyl, pyridazinyl, thienyl, furyl, oxazolyl, thiazolyl, benzooxazolyl, imidazolyl, indolyl, quinolyl, isoquinolyl, thiazolyl, benzothlazolyl, benzoxazolyl and pyrrolyl. The especially preferred heteroaryl groups include thienyl, pyrazinyl, pyrimidinyl, pyridyl, thiazolyl, and the N-oxide of pyridyl.

As defined herein, R is an alkyl group, an aryl group, lower arylalkyl group, lower cycloalkyl, alkyl heterocyclic or heterocyclic lower alkyl.

The aryl group defined for R is as defined hereinabove.

As defined herein, the "heterocyclic" group, when used alone or in combination, is a nitrogen, sulfur, or oxygen containing heterocyclic group. More specifically, the heterocyclic group contains at least 1 ring heteroatom. The ring heteroatoms are either oxygen, sulfur or nitrogen and may contain up to four ring heteroatoms. The heterocyclic group may be monocyclic, bicyclic or polycyclic, but if the heterocyclic group contains more than one ring, the rings are fused. The heterocyclic group contains 1–4 ring heteroatoms, from 5–14 ring atoms and from 1–13 and preferably 3–13 ring carbon atoms and up to a total of 18 carbon atoms. The heterocyclic groups includes the heteroaryl group defined hereinabove and the benzoheterocyclics. This group also includes the fully saturated or partially saturated heterocyclics. The heterocyclic group includes such groups as those specifically enumerated in the preceding paragraph as well as imidazolidinyl, imidazolinyl, pyrazolidinyl, pyrazolinyl, piperidyl, piperazinyl, indolinyl, tetrahydrofuryl, morpholinyl and the like. Preferred heterocyclic groups include the preferred heteroaryl groups enumerated above.

The "alkyl" groups, when used alone or in combination with other groups, are lower alkyl containing from 1 to 6 carbon atoms and may be straight chain or branched. These groups include methyl, ethyl, propyl, isopropyl, butyl, isobutyl, tertiary butyl, pentyl, hexyl, and the like. The preferred alkyl group is methyl.

The term cycloalkyl when used alone or in combination is a cycloalkyl group containing from 3 to 18 ring carbon atoms and up to a total of 25 carbon atoms. The cycloalkyl groups may be monocyclic, bicyclic, or polycyclic and if more than 1 ring is present, the rings are fused. The cycloalkyl group may be completely saturated or partially saturated. Examples include cyclopropyl, cyclobutyl, cyclopentyl, cyclohexyl, cycloheptyl, cyclooctyl, cyclodecyl, cyclohexenyl, cyclopentenyl, cyclooctenyl, cycloheptenyl, decalinyl, hydroindanyl, indanyl, fenchyl, pinenyl and adamantyl, and the like. The preferred cycloalkyl is pentyl and hexyl.

The "aryl lower alkyl" group is an alkyl group which is substituted by an aryl group. Examples include benzyl, phenethyl, phenpropyl, diphenylmethyl, 1,2-diphenylethyl, 1,1-diphenylmethyl and the like. The preferred group is benzyl.

The "heterocyclic lower alkyl" group is an alkyl group substituted by a heterocyclic group, as defined and enumerated hereinabove.

The "cycloalkyl lower alkyl" group is an alkyl group which is substituted by a cycloalkyl group, as defined and enumerated hereinabove.

As indicated hereinabove, the Ar and R groups can be substituted by an electron withdrawing and electron donating groups. The terms "electron withdrawing" and "electron donating" refer to the ability of a substituent to withdraw or to donate electrons relative to that of hydrogen if the hydrogen atom occupied the same position on the molecule. These terms are well understood by one skilled in the art and are discussed in *Advanced Organic Chemistry*, by J. March, John Wiley & Sons, New York, New York, pp. 16–18 (1985) and the discussion therein is incorporated herein by reference. Electron withdrawing groups include halo (e.g., bromo, fluoro, chloro, oiodo), nitro, carboxy, lower carbalkoxy, carboxamido, N-loweralkylcarboxamido, N,N-lower dialkyl carboxamido, formyl, lower alkanoyl, lower alkenyl, lower alkynyl, aryl, heterocyclic, ammonium, including mono, di-, or tri-alkylammonium, trifluoromethyl, $SO_2CF_3$ cyano, sulfonyl, sulfinyl and the like. The preferred electron withdrawing groups are carboxy, ammonium, NO, $N_2^+$, $SO_2CF_3$, halo and especially nitro. Electron donating groups include such groups as hydroxy, lower alkoxy, including methoxy, ethoxy and the like; amino, lower alkylamino; di(loweralkylamino); aryloxy, such as phenoxy, mercapto, lower alkythio, lower alkylmercapto, and the like. One skilled in the art will appreciate that the aforesaid substituents may have electron donating or electron withdrawing properties under different chemical conditions.

As defined herein, Y is a chemical bond or $(CR_3R_4)_p$. It is preferred that Y is a chemical bond. However, when p is 1 or 2, it is preferred that $R_3$ and $R_4$ are hydrogen or alkyl containing 1–3 carbon atoms. The preferred alkyl group for $R_3$ and $R_4$ is methyl. It is especially preferred that $R_3$ and $R_4$ are hydrogen.

Although p may range from 1–2, the preferred value of p is 1.

The preferred value of Ar is phenyl. When Ar is heterocyclic, it is preferred that the ring hetero atom is α to the carbon atom to which the "X" moiety is bonded. For purposes of this context only it is assumed that the 1-position of the heterocyclic moiety is that position to which the bridging unit is attached and the α-position is that position in the ring which is adjacent thereto. When Ar is heterocyclic, including heteroaryl, it is preferred that the heteroatom is on the α-position of the ring. A nitrogen containing heteroaryl containing up to 10 ring atoms and two, and preferably one nitrogen ring atom is especially preferred. Examples of these heteroaryls include thiazolyl, pyridyl, primidinyl, pyrazinyl, benzoxazoly and the N-oxide of pyridyl. The especially preferred value of Ar is phenyl.

The preferred value of R is phenyl or heterocyclic. It is especially preferred that R is phenyl. When R is heterocyclic, however, it is preferred that the ring heteroatom is on the a-position of the ring. The preferred heterocyclic is heteroaryl, especially the nitrogen or sulfur-containing heteroaryl group. The preferred heteroaryl contains two, and preferably one ring nitrogen atom or one sulfur ring atom. Examples of the preferred heteroaryl groups for R are thiazolyl, pyridyl, pyrimidinyl, pyrazinyl, benzooxazolyl and the N-oxide of pyridyl.

The preferred value of X is $SO_2$, $SO_2O$, $CR_5=CR_6$, SO, S, HC=CCOOH, O, H,

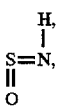

$SeO_2$, Se and SeO. Especially preferred values of X include O, $SO_2O$, SO, $SO_2$, S,

and SeO. It is especially preferred that X is $SO_2$.

The preferred value of $R_1$ is nitro or hydrogen, or ammonium. In the case when Ar is aryl, it is especially preferred that $R_1$ is substituted on the carbon ring atoms that is α to the bridging group. For example, if Ar is phenyl, it is preferred that $R_1$ is in the ortho position. The preferred value of $R_2$ is hydrogen, lower alkyl, especially methyl, carboxy, carbalkoxy, halo, especially chloro, nitro carboxamido and mono, di or tri haloalkyl, especially trifluoromethyl. The especially preferred value of $R_2$ is hydrogen or nitro.

It is preferred that n is O, i.e., the only substituent on Ar is $R_1$.

It is preferred that $T_1$ is substituted on the carbon ring atom that is α to the bridging group.

The preferred value of $T_1$ is hydrogen, lower alkyl or an electron withdrawing group. A more preferred value of $T_1$ is hydrogen, nitro, lower alkyl, especially methyl, halo, e.g., chloro, carboxy, carbalkoxy, carboxamide. It is most preferred that $T_1$ is hydrogen methyl, chloro, nitro, nitrosyl, or carboxy. Especially preferred is hydrogen, nitro or carboxy. The most especially preferred value of $T_1$ is hydrogen or nitro.

It is preferred that $T_2$ is an electron withdrawing group, hydrogen or lower alkyl. Preferred values of $T_2$ are hydrogen, halo, e.g., nitro, chloro, and lower alkyl, e.g., methyl. The preferred value of $T_2$ is hydrogen.

It is preferred that n is O, i.e., the only substituent on R is $T_1$. When either Ar or R is phenyl and any one of $T_1$, $T_2$, $R_1$ and $R_2$ are nitro, it is preferred that the nitro substituent is not on the para position of the phenyl.

It is preferred that G is lower alkyl, aryl, aryl lower alkyl, heterocyclic or heterocyclic lower alkyl.

An embodiment of the present invention has the formula

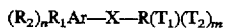

wherein $R_2$, $R_1$, Ar, X, R, $T_1$, $T_2$, n and m are as defined hereinabove.

In a preferred formulation, both Ar and R may each be independently heteroaryl or aryl. In a more preferred embodiment, either Ar or R is phenyl. In the most preferred embodiment, both Ar and R are phenyl.

Another embodiment of the present invention has the formulae:

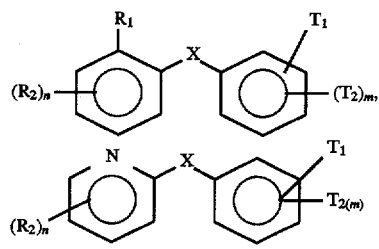

wherein $R_1$, $R_2$, $T_1$, $T_2$, X, n and m are as defined hereinabove.

The preferred value of X in these formule are S, SO, or $SO_2$ and

Especially preferred is SO and $SO_2$. The most preferred value of X is $SO_2$. It is preferred that n and m are 1, and that $R_2$ and $T_2$ are each independently hydrogen or an electron withdrawing group. It is especially preferred that $R_1$ is nitro, hydrogen or ammonium. Furthermore, if any one $R_1$ ($R_2$), $T_1$ and ($T_2$) are nitro, it is preferred that the nitro substituent is in the ortho or meta positions.

Another embodiment of the present invention has the formula

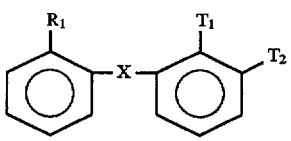

wherein X, $R_1$, $R_2$, $T_1$, $T_2$, n and m are as defined herein. The preferred values of X in this formula are S, SO, and $SO_2$ and

Especially preferred is SO and $SO_2$. It is preferred that n and m are 1 and $R_2$ and $T_2$ are each independently hydrogen or an electron withdrawing group. It is preferred that $R_1$ is nitro, hydrogen, or ammonium.

Another embodiment of the present invention has the formula

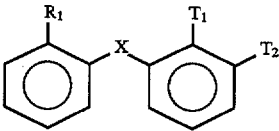

wherein $R_1$ is H, $NO_2$, $NH_2$, $NH_3^+$, NHOH or HO;

X is $SO_2$, SO or S;

$T_1$ is H, $NO_2$, $NH_2$, $NH_3^+$, NHOH or NO and $T_2$ is H, $CH_3$ and $OCH_3$.

An embodiment of the present invention is

[Structure: phenyl ring with $R_1$ substituent, connected via X to another phenyl ring with $T_2$ substituent]

wherein $R_1$ is H, $NO_2$, $NH_2$, $NH_3^+$ NHOH or NO,
$T_2$ is H, $CH_3$ or $OCH_3$ and
X is $SO_2$ When X is SO, an embodiment of the present invention has the formula

[Structure: phenyl ring with $R_1$ substituent, connected via X to another phenyl ring with $T_2$ substituent]

wherein $R_1$ and $T_2$ are independently H, $NO_2$, $NH_2$, $NH_3^+$, NHOH and NO and
X is SO.

Another embodiment of the present invention has the formula

[Structure: phenyl ring connected via $S(O_2)$ to another phenyl ring with $T_1$ and $T_{2(m)}$ substituents]

wherein $T_1$, $T_2$ and more as defined herein.

A further embodiment of the present invention has the formula

[Structure: phenyl ring with $R_1$ and $R_2$ substituents, connected via X to another phenyl ring with $T_1$ and $T_2$ substituents]

wherein X, $R_1$, $R_2$, $T_1$ and $T_2$ are as defined hereinabove.

In the most preferred embodiment, X is $SO_2$, $R_1$, $R_2$, $T_1$ and $T_2$ are $NO_2$.

The present invention contemplates all combinations and permutations of R, $R_1$, $T_1$, $T_2$, Ar, $R_1$, n and m as defined herein.

The compounds of the present invention can be prepared by art-recognized methodology using starting materials that are commercially available of readily prepared. For example, compounds of the present invention can be prepared by nucleophile substitution according to the following equation:

$$R_1(R_2)Ar-L + {}^-X-Y\ R(T_1)(T_2)_m \longrightarrow I$$
$$\text{II} \quad\quad \text{III}$$

wherein $R_1$, $R_2$, X, Y, R, $T_1$, $T_2$, n and m are as defined hereinabove and L is a leaving group, such as halogen, e.g., bromo, chloro and the like. A salt, such as potassium ethyl xanthate can additionally be present to facilitate the coupling as, for example, in the case when Ar is pyridyl. Alternatively, a compound of Formula I may be formed by reacting $$R_1(R_2)_nAr-X-L + Y-R(T_1)(T_2)_m \rightarrow I$$

wherein $R_1$, $R_2$, Ar, X, L, Y, R, $T_1$, $T_2$, n and m are defined hereinabove. For example, when X is S, the compounds of the present invention can be prepared by reacting a compound of Formula II with $-S-Y-R(T_1)(T_2)$ under nucleophilic substitution conditions. The reaction may be run in an inert solvent such as ethanol, DMF, DMSO, $Me_2SO$, or HMPT. The reaction mixture is heated at a temperature sufficient to effect the nucleophilic substitution conditions. The temperature ranges from 50° C. to the refluxing temperature of the solvent. As an example, 1-nitro-2-(phenylthio)benzene was prepared by reacting thiophenol in the presence of a base with 2-chloronitrobenzene in hot ethanol.

The sulfoxide can be prepared in accordance with the procedure described in U.S. Pat. No. 4,831,194 to Kriedl et al., which is incorporated herein by reference. More specifically, a sulfinyl halide of Formula IV is reacted with the compound of Formula V as shown hereinbelow:

$$(R_1)(R_2)_nAr-SO-Hal + Y-R(T_1)(T_2)_m \longrightarrow I, X=SO$$
$$\text{IV}$$

wherein $R_1$, $R_2$, Ar, Y, R, $T_1$, $T_2$, n and m are defined hereinabove and Hal is halide. The compound of Formula IV can be prepared by reacting an arylsulfonyl halide (V) with an alkali metal sulfite ($MSO_2$) followed by acid addition; and halogenating the product thereof:

$$(R_1)(R_2)_nAr-SO_2-Hal \xrightarrow[\text{2. H}]{\text{1. }M_2SO_3}$$
$$\text{V}$$

$$R_1(R_2)_nArSO_2H \xrightarrow{\text{halogenating agent}} IV$$

An exemplary procedure for the preparation of the sulfonyl compound is as follows:

$$(R_1)(R_2)_nAr-Hal + {}^-SO_2-Y-R(T_1)(T_2)_m \xrightarrow{\text{Cu}} I$$
$$\text{VI} \quad\quad \text{VII}$$

where X is $SO_2$ wherein $R_1$, $R_2$, Ar, Hal, Y, R, $T_1$, $T_2$, n and m are as defined hereinabove. The aryl halide (VI) is reacted with the sulfonate (VII) in the presence of a copper catalyst. The reaction mixture is heated at temperatures ranging from 50°–250° C., and preferably at about 180° C., to form the product.

Alternatively, the sulfoxide and the sulfones can be prepared from the corresponding thiols. For example, one mole of the compound of Formula I wherein X is S is reacted with one mole of an oxidizing agent, such as 30% $H_2O_2$, $NaIO_4$, t-BuO—Cl, acyl nitrite, peracids, sodium perborates and the like, to form the corresponding sulfoxides. The sulfoxide in turn can be further oxidized to the corresponding sulfones by reacting the sulfoxide with another mole of an oxidizing agent, such as 30% $H_2O_2$, $KMnO_4$, potassium hydrogen persulfate, sodium perborate and the like, to form the corresponding sulfone. If excess oxidizing agent were present, then the sulfide can be directly converted to the sulfone without isolation of the sulfoxide.

The sulfonic acid ester can be prepared by reacting the halide of Formula II, i.e., where L is halide and $R_1$, $R_2$, Ar and n are as defined herein with $(T_1)(T_2)_mR-Y-SO_3^-$ under nucleophilic substitution conditions as described herein.

Alternatively, the sulfonic ester can be prepared by reacting the sulfonyl halide of Formula VIII with an alcohol (or phenol) of Formula IX under esterification conditions

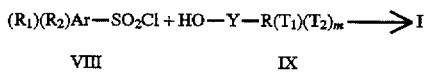

The selenium compounds, i.e., compounds in which X is Se, SeO, SeO$_2$, or SeO$_3$, can be prepared in an analogous fashion to the corresponding sulfur compounds, i.e., S, SO, SO$_2$ or SO$_3$, respectively, that are described herein.

An exemplary procedure for preparing amine compounds in which X is NH is by reacting a compound of Formula II wherein L is a halo, such as bromo or chloro, with H$_2$N—Y—R(T$_1$)(T$_2$)$_m$ in the presence of a base, such as sodium carbonate, and optionally in the presence of a copper catalyst.

Compounds in which X is O can be prepared by the following exemplary procedure. The salt of an alcohol (or phenol) of Formula X is reacted with the compound of Formula II wherein L is halo, e.g. bromo or chloro under nucleophilic substitution reactions.

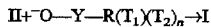

An exemplary procedure for preparing a sulfonamide, i.e., compounds in which X is SO$_2$NH$_2$ is by reacting a sulfonyl halide of the fomula V, e.g. where Hal is chloro, with an amine of the formula H$_2$N—Y—(R)(T$_1$)(T$_2$) under substitution reaction conditions.

The compounds in which X is

can be prepared by techniques known to one skilled in the art. An exemplary porcedure is as follows.

Oxidation of the sulfoxide prepared hereinabove with hydrazoic acid (HN$_3$) generate the compound of the present invention in which X is

Alternatively, the sulfoximine (compounds of the present invention in which X is

are prepared by oxidizing the corresponding sulfinimine (S=NH) with hydrogen peroxide.

As in many organic reactions, inert solvents in the above reactions can be employed such as methanol, ethanol, propanol, acetone, tetrahydrofuran, dioxane, dimethylformamide, dichloromethane, chloroform, and the like. The reactions are normally effected at or near room temperature, although temperatures ranging from 50° C. up to the reflux temperature of the reaction mixture can be employed.

The various substituents on the compounds, e.g. as defined in R$_1$, R$_2$, T$_1$ and T$_2$ can be present in the starting compounds, added to any one of the intermediates or added after formation of the final products by the known methods of substitution or conversion reactions. For example, the nitro groups can be added to the aromatic ring by nitration and the nitro group converted to other groups, such as amino by reduction, and halo by diazotization of the amino group and replacement of the diazo group. Alkanoyl groups can be substituted onto the aryl groups by Friedel-Crafts acylation. The acyl groups can be then transformed to the corresponding alkyl groups by various methods, including the Wolff-Kishner reduction and Clemmenson reduction. Amino groups can be alkylated to form mono, dialkylamino and trialkylamino groups; and mercapto and hydroxy groups can be alkylated to form corresponding thioethers or ethers, respectively. Primary alcohols can be oxidized by oxidizing agents known in the art to form carboxylic acids or aldehydes, and secondary alcohols can be oxidized to form ketones. Thus, substitution or alteration reactions can be employed to provide a variety of substituents throughout the molecule of the starting material, intermediates, or the final product.

In the above reactions, if the substituents themselves are reactive, then the substituents can themselves be protected according to the techniques known in the art. A variety of protecting groups known in the art may be employed. Examples of many of these possible groups may be found in "Protective Groups in Organic Synthesis," by T. W. Greene, John Wiley & Sons, 1981.

Resulting mixtures of isomers can be separated in the pure isomers by methods known to one skilled in the art, e.g., by fractional distillation, crystallization and/or chromotagraphy.

The active ingredients of the therapeutic compositions and the compounds of the present invention exhibit excellent- anti-retrovirus activity when administered in amounts ranging from about 10 mg to about 100 mg per kilogram of body weight per day. A preferred dosage regimen for optimum results would be from about 20 mg to about 50 mg per kilogram of body weight per day, and such dosage units are employed that a total of from about 1.0 gram to about 3.0 grams of the active compound for a subject of about 70 kg of body weight are administered in a 24-hour period. This dosage regimen may be adjusted to provide the optimum therapeutic response and is preferably administered one to three times a day in dosages of about 600 mg per administration. For example, several divided doses may be administered daily or the dose may be proportionally reduced as indicated by the exigencies of the therapeutic situation. A decided practical advantage is that the active compound may be administered in an convenient manner such as by the oral, intraveneous, intramuscular or subcutaneous routes.

The active compound may be orally administered, for example, with an inert diluent or with an assimilable edible carrier, or it may be enclosed in hard or soft shell gelatin capsule, or it may be compressed into tablets, or it may be incorporated directly with the food of the diet. For oral therapeutic administration, the active compound may be incorporated with excipients and used in the form of ingestible tablets, buccal tablets, troches, capsules, elixirs, suspensions, syrups, wafers, and the like. Such compositions and preparations should contain at least 1% of active compound. The percentage of the compositions and preparations may, of course, be varied and may conviently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 5 and 1000 mg of active compound.

The tablets, troches, pills, capsules and the like may also contain the following: A binder such as gum tragacanth, acacia, corn starch or gelatin; excipients such as dicalcium phosphate; a disintergrating agent such-as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the acitve compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed.

The active compound may also be administered parenterally or intraperitoneally. Dispersions can also be prepared in glycerol, liquid polyethylene glycols, and mixtures thereof and in oils- Under ordinary conditions of storage and use, these preparations contain a preservative to prevent the growth of microorganisms.

The pharmaceutical forms suitable for injectable use include sterile aqueous solutions (where water soluble) or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating such as lecithin; by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of Preparation are vacuum drying and the freeze-drying technique which yield a powder of the active ingredient plus any additional desired ingredient from previously sterile-filtered solution thereof.

As used herein, "pharmaceutically acceptable carrier" includes any and all solvents, dispersion media, coatings, antibacterial and antifungal agents, isotonic and absorption delaying agents, and the like. The use of such media and agents for pharmaceutical active substances is well known in the art. Except insofar as any conventional media for agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier. The specification for the novel dosage unit forms of the invention are dictated by and directly, dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically acceptable carrier in dosage unit form as hereinbefore disclosed. A unit dosage form can, for example, contain the principal active compound in amounts ranging from about 5 to about 1000 mg, with from about 250 to about 750 mg being preferred. Expressed in proportions, the active compound is generally present in from about 10 to about 750 mg/ml of carrier. In the case of compositions containing supplementary active ingredients, the dosages are determined by reference to the usual dose and manner of administration of the said ingredients.

For a better understanding of the present invention together with other and further objects, reference is made to the following descriptions and examples. These examples are provided solely for illustrative purposes. Therefore, the invention is not to be limited in any way by the exemplification.

EXAMPLE 1

1-Nitro-2-(phenylthio)benzene

The following procedure served as the model for the formation of all compounds of this type required by this study. 2-Chloronitrobenzene (25.0 g, 0.16 mol) in 80 mL of hot ethanol was added to a mixture of thiophenol (17.60 g, 0.16 mol), $Na_2CO_3$ (20.8 g, 0.224 mol), and 70 mL of $H_2O$ and the whole was stirred and heated to boiling for 2 h. The reaction mixture was then poured into 275 mL of ice-water to precipitate a dark yellow solid. The crude 1-nitro-2-(phenylthio)benzene, mp 76°–78° C., was recrystallized from 95% ethanol to afford 33.3 g (90%) of bright yellow crystals, mp 78.5°–80° C. (lit. mp 78°–80° C.). IR (KBr) 1500 and 1334 $cm^{-1}$ ($NO_2$); $^1H$ NMR ($CDCl_3$) δ 8.5 (m, 1 H), 7.35 (m, 7 H) and 6.75 (m, 1 H).

EXAMPLE 2

1-[(4-Methylphenyl)thio]-2-nitrobenzene

This compound was prepared by the model procedure from the following compounds: 4-Methylthiophenol (12.40 g, 0.10 mol), $Na_2CO_3$ (14.80 g, 0.14 mol), and 2-chloronitrobenzene (15.7 g, 0.10 mol). The crude product, mp 85°–87° C., was recrystallized from alcohol to afford 22.30 g (91%) of brilliant yellow needles, mp 89°–90° C. (lit.

mp 89°–90° C.). IR (KBr) 3062 (C—H), 1510 and 1334 (NO$_2$), and 1458 cm$^{-1}$ (CH$_3$); $^1$H NMR (CDCl$_3$) δ 8.15 (m, 1 H), 7.25 (m, 6 H), 6.75 (m, 1 H) and 2.35 (s, 3 H).

EXAMPLE 3

1-[(4-Chlorophenyl)thio]-2-nitrobenzene

This compound was synthesized by the model procedure from the following compounds: 4-Chlorothiophenol (15.0 g, 0.10 mol), Na$_2$CO$_3$ (15.50 g, 0.15 mol), and 2-chloronitrobenzene (16.3 g, 0.10 mol). The crude product, mp 91°–93° C., was recrystallized from alcohol to afford 25.0 g (91%) of yellow crystals, mp 94°–95° C. (lit. mp 94° C.). IR(KBr) 3050 (C—H), 1512 and 1336 cm$^{-1}$ (NO$_2$); $^1$H NMR (CDCl$_3$) δ 8.2 (m, 1 H) and 7.45 (m, 7 H).

EXAMPLE 4

1-Nitro-2-(phenylsulfonyl)benzene (1)

The following procedure served as the model for all compounds of this type required by this study. 1-Nitro-2-(phenylthio)benzene (6.50 g, 28.0 mmol) was added to 40 mL of acetic acid in a flask equipped with a magnetic stirrer. The mixture was heated to 90° C. To the stirred, warm acetic acid solution, 12.5 mL (0.12 mol) of 30% hydrogen peroxide was added slowly over a 15-min period. After 1 h at 90° C., the reaction mixture was heated to boiling and water was added until the solution became turbid. The solution was cleared by adding acetic acid and then cooled slowly to room temperature. The white needles that crystallized were separated by suction filtration and allowed to dry. The yield of 1-nitro-2-(phenylthio)benzene was 7.05 g (95%), mp 145°–146.5° C. (lit.$^{49}$ mp 146°–147° C.). IR (KBr) 3085 (C—H), 1547 and 1320 (NO$_2$), and 1319 and 1157 cm$^{-1}$ (SO$_2$); $^1$H NMR (CDCl$_3$) δ 8.2 (m, 1 H) and 7.65 (m, 8 H).

EXAMPLE 5

1-(4-Methylphenylsulfonyl)-2-nitrobenzene (2)

This compound was prepared by the model procedure from 1-[(4-methylphenyl)thio]-2-nitrobenzene (7.00 g, 29.0 mmol), 30% H$_2$O$_2$ (12.0 mL, 0.12 mol), and 50 mL of acetic acid. The yield of nitrosulfone was 7.20 g (91%), mp 155°–156° C. (lit. mp 156°–157° C.). After several weeks of storage in a clear glass bottle, the sulfone turned light green. IR (KBr) 3085 and 2950 (C—H), 1546 and 1322 (NO$_2$), 1320 and 1158 cm$^{-1}$ (SO$_2$); $^1$H NMR (CDCl$_3$) δ 7.75 (m, 8 H) and 2.4 (s, 3 H).

EXAMPLE 6

1-(4-chlorophenylsulfonyl)-2-nitrobenzene (36)

This compound was prepared by the model procedure from 1-[(4-chlorophenyl)thio]-2-nitrobenzene (7.00 g, 26.0 mmol), 30% H$_2$O$_2$ (11.0 mL, 0.11 mol), and 40 mL of acetic acid. The yield of sulfone was 7.00 g (90%), mp 136.5°–137.5° C. (lit. mp 137°–138° C.). IR (KBr) 3087 (C—H), 1543 and 1324 (NO$_2$), 1318 and 1159 cm$^{-1}$ (SO$_2$); $^1$H NMR (CDCl$_3$) δ 8.15 (m, 1 H) and 7.6 (m, 7 H).

EXAMPLE 7

Using the procedures described herein, the following compounds can be prepared:

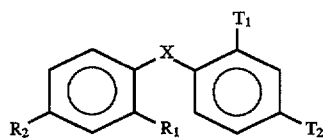

| COMPOUND NUMBER | R$_1$ | R$_2$ | T$_1$ | T$_2$ | X |
|---|---|---|---|---|---|
| 3 | H | H | H | H | SO$_2$ |
| 4 | NO$_2$ | H | H | Cl | SO$_2$ |
| 5 | NO$_2$ | H | NO$_2$ | H | S |
| 6 | NO$_2$ | H | NO$_2$ | H | SO$_2$ |
| 7 | —N* | H | H | H | SO$_2$ |

*Pyridine ringe with N at position R$_1$

EXAMPLE 8

Other compounds can be prepared by the procedures described herein:

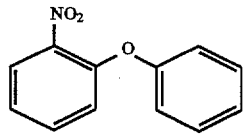
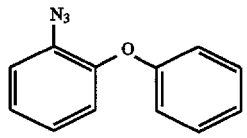
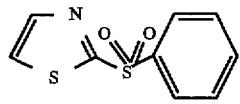
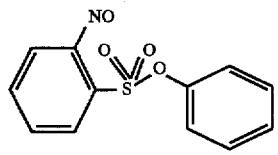
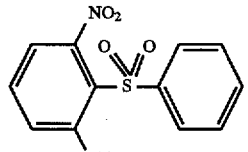
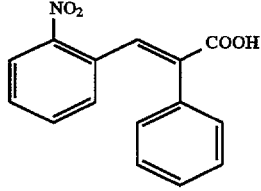
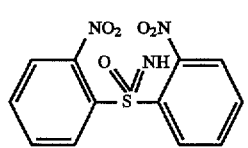

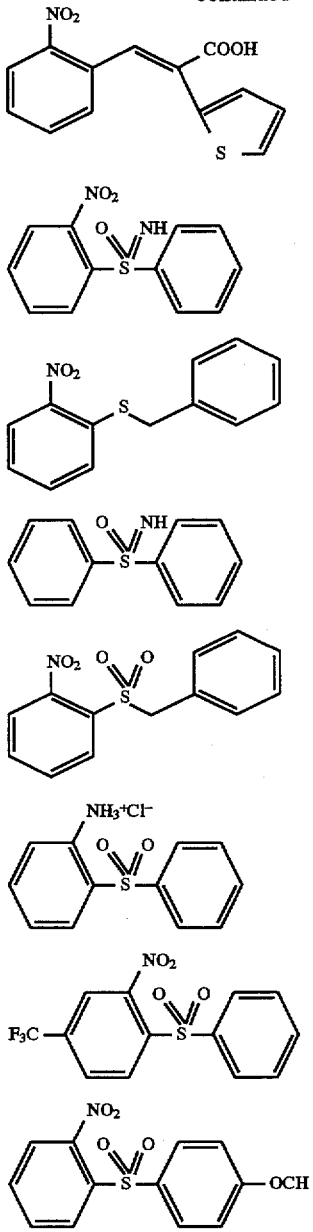

The compounds of the present invention are effecitve in treating diseases attributable to retroviruses such as AIDS or ARC in animals, such as mammals. These compounds are cabable of retarding the progression of retroviruses. Further, they are capable of retarding the growth and/or replication of the retrovirus. These compounds are believed to retard the progression of the retrovirus infections attributable to HTLV-1, HTLV-2 or Lentivirus. Included in the class of Lentivirus in which compounds of the present invention are extremely effective are HIV-1, HIV-2, SIV or medi-vesni. Thus, compounds of the present invention are useful in treating AIDS or AIDS related complex (ARC) and to ameliorate or improve the condition in the animal afflicted with the retrovirus.

To determine the effectiveness of the compounds of the present invention, various assays, approved by the N.C.I. have been developed.

One such method is used to determine the effectiveness of representative compounds and compositions of the present invention in the Rauscher and LP-BMS Murine Leukemia Virus (MLV) In Vitro Assays.

In accordance with the procedure

SC-1 cells were grown as monolayers in 6-well tissue culture plates (Falcon). The a test compound was added to the cultures at the time of virus inoculation (approximately 24 hours after the cells were seeded) and was present for 3 days, at which time the cultures were irradiated with UV light. All compounds were solubilized in DMSO prior to dilution in grown medium. The highest concentration of DMSO present in the cultures was 0.05%. The test cultures (triplicate cultures per drug concentrate) each contained 2 ml of test compound diluted in growth medium (Eagle's minimum) essential medium (EMEM) supplemented with 5% heat-inactivated fetal bovine serum (FBS) and 0.5 ml of the virus suspension diluted to produce a countable number of plaques per well. The six virus control cultures contained 2 ml of medium and 0.5 ml of the virus suspension. NSC606170(ddC) was included as a positive control. drug. Drug cytotoxicity control cultures ( containing test compound) but no virus and cell control culture (containing no test compound) or virus were included in the assay. On day 3 post-virus inoculation, the cultures were irradiated and XC cells were added. Three days after V-irradiation, the cultures were fixed with formalin and stained with 0.1% crystal violet. The plaques were counted with the aid of a dissection microscope.

A dye conversion assay to determine drug-induced cytotoxicity was performed. This assay is based on the conversion of MTT to a formazan product in living cells. This conversion results in a color change which can be detected spectrophotometrically. A 96-well tissue culture plate was seeded with $1.4 \times 10$ SC-1 cells per well at the time that the 6-well plates were seeded for the UV-XC plaque assay. The following day, the medium was decanted and the cell control cultures received 100 ul of medium. The drug controls received 80 ul of drug and 20 ul of medium such that the final concentration of drug was equivalent to that used in the 6-well plates. On day 3 after addition of the drug, 50 ul of a 2 mg/ml solution of MTT in EMEM with 5% heat-inactivated FBS were added each well. The culture was incubated for 7 hours and 100 ul of a 10% SDS: 0.01 N HCL solution was added to each well. The culture was incubated overnight and the following morning the optical density (O.D.) was read at 570 nm wavelength on a Perkin-Elmer spectrophotometer. The percent reduction in the drug-treated cell. O.D. reading compared to the control cell O.D. reading was calculated.

Using the procedure, the following data is generated from representative compounds of the presnet invention.

| Compound Concentration | i. Data from Rauscher MuLV assay Data from Formazon assay: | | | | |
|---|---|---|---|---|---|
| | Plaque #1 | Count #2 | Replicate #3 | Mean Count | % Plaque Reduction |
| Test Compound 1 | | | | | |
| $1 \times 10^{-3}$ M | T | T | T | T | — |
| $1 \times 10^{-4}$ M | 43 | 48 | 46 | 46 | 26% |
| $1 \times 10^{-5}$ M | 58 | 42 | 60 | 53 | 14% |
| $1 \times 10^{-6}$ M | 71 | 43 | 53 | 56 | 10% |
| $1 \times 10^{-7}$ M | 53 | 69 | 71 | 64 | 0% |
| $1 \times 10^{-8}$ M | 64 | 55 | 76 | 65 | 0% |

Test Compound 2

| | | | | | |
|---|---|---|---|---|---|
| $1 \times 10^{-3}$ M | 20 | 20 | 17 | 19 | 69% |
| $1 \times 10^{-4}$ M | 9 | 8 | 8 | 8 | 87% |
| $1 \times 10^{-5}$ M | 60 | 69 | 64 | 64 | 0% |
| $1 \times 10^{-6}$ M | 72 | 53 | 5 | 61 | 2% |
| $1 \times 10^{-7}$ M | 52 | 57 | 60 | 56 | 9% |
| $1 \times 10^{-8}$ M | 62 | 56 | 63 | 60 | 3% |

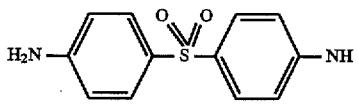

| | | | | | |
|---|---|---|---|---|---|
| $1 \times 10^{-3}$ M | 0 | 0 | 0 | 0 | 100% |
| $1 \times 10^{-4}$ M | 0 | 0 | 0 | 0 | 100% |
| $1 \times 10^{-5}$ M | 24 | 27 | 26 | 26 | 59% |
| $1 \times 10^{-6}$ M | 51 | 43 | 47 | 47 | 24% |
| $1 \times 10^{-7}$ M | 74 | 72 | 67 | 71 | 0% |
| $1 \times 10^{-8}$ M | 79 | 65 | 62 | 69 | 0% |
| Virus Control | 73 | 54 | 57 | 62 | |
| | 55 | 67 | 66 | | | ii. Data from LP-BM5 MuLV assay

Test Compound 1

| | | | | | |
|---|---|---|---|---|---|
| $1 \times 10^{-3}$ M | T | T | T | T | — |
| $1 \times 10^{-4}$ M | 219 | 216 | 328 | 254 | 11% |
| $1 \times 10^{-5}$ M | 335 | 216 | 232 | 261 | 9% |
| $1 \times 10^{-6}$ M | 337 | 218 | 210 | 255 | 11% |
| $1 \times 10^{-7}$ M | 201 | 192 | 228 | 207 | 27% |
| $1 \times 10^{-8}$ M | 222 | 204 | 311 | 246 | 14% |

Test Compound 2

| | | | | | |
|---|---|---|---|---|---|
| $1 \times 10^{-3}$ M | 162 | 123 | 104 | 130 | 55% |
| $1 \times 10^{-4}$ M | 43 | 37 | 70 | 50 | 82% |
| $1 \times 10^{-5}$ M | 265 | 204 | 267 | 245 | 14% |
| $1 \times 10^{-6}$ M | 270 | 217 | 304 | 264 | 8% |
| $1 \times 10^{-7}$ M | 327 | 269 | 301 | 299 | 0% |
| $1 \times 10^{-8}$ M | 299 | 340 | 314 | 318 | 0% |

Compound 37

| | | | | | |
|---|---|---|---|---|---|
| $1 \times 10^{-3}$ M | 0 | 0 | 0 | 0 | 100% |
| $1 \times 10^{-4}$ M | 0 | 0 | 0 | 0 | 100% |
| $1 \times 10^{-5}$ M | 135 | 103 | 150 | 129 | 55% |
| $1 \times 10^{-6}$ M | 320 | 346 | 321 | 329 | 0% |
| $1 \times 10^{-7}$ M | 220 | 236 | 216 | 224 | 22% |
| $1 \times 10^{-8}$ M | 196 | 351 | 287 | 278 | 3% |
| Virus Control | 317 | 209 | 195 | 286 | |
| | 350 | 325 | 318 | | | iii. Data from Cytotoxicity Assay

| Compound Concentration | O.D. Reading | % of Control | % Reduction |
|---|---|---|---|
| Test Compound 1 | | | |
| $1 \times 10^{-3}$ M | 0.851 | 55% | 45% |
| $1 \times 10^{-4}$ M | 1.320 | 85% | 15% |
| $1 \times 10^{-5}$ M | 1.504 | 97% | 3% |
| $1 \times 10^{-6}$ M | 1.522 | 98% | 2% |
| $1 \times 10^{-7}$ M | 1.566 | 101% | 0% |
| $1 \times 10^{-8}$ M | 1.530 | 99% | 1% |
| none | 1.549 | | |
| Test Compound 2 | | | |
| $1 \times 10^{-3}$ M | 1.066 | 69% | 31% |
| $1 \times 10^{-4}$ M | 1.345 | 87% | 13% |
| $1 \times 10^{-5}$ M | 1.425 | 92% | 8% |
| $1 \times 10^{-6}$ M | 1.418 | 92% | 8% |
| $1 \times 10^{-7}$ M | 1.429 | 92% | 8% |
| $1 \times 10^{-8}$ M | 1.411 | 91% | 9% |
| none | 1.549 | | |
| Compound 37 (ddC) | | | |
| $1 \times 10^{-3}$ M | 1.180 | 75% | 25% |
| $1 \times 10^{-4}$ M | 1.544 | 98% | 2% |
| $1 \times 10^{-5}$ M | 1.493 | 95% | 5% |
| $1 \times 10^{-6}$ M | 1.519 | 96% | 4% |
| $1 \times 10^{-7}$ M | 1.564 | 99% | 1% |
| $1 \times 10^{-8}$ M | 1.544 | 98% | 2% |
| none | 1.577 | | |

Another assay for testing the efficacy of the compounds is the procedure* used in the National Cancer Institute's test for agents active against Human Immunodeficiency Virus (HIV). It is designed to detect agents acting at any stage of the virus reproductive cycle. The assay basically involves the killing of T4 lymphocytes by HIV. Small amounts of HIV are added to cells, and a complete cycle of virus reproduction is necessary to obtain the required cell killing. Agents that interact with virions, cells, or virus gene-products to interfere with viral activities will protect cells from cytolysis. The system is automated in several features to accommodate large numbers of candidate agents and is generally designed to detect anti-HIV activity. However, compounds that degenerate, or are rapidly metabolized in the culture conditions may not show activity in this screen. All tests are compared with at least one positive (e.g., AZT-treated) control done at the same time under identical conditions.

* Weislow. O. W., Kiser, R., Fine, D., Bader, J., Shoemaker, R. H., Boyd, M. R.: New soluble-formazan assay for HIV-1 cytopathic effects: application to high-flux screening of synthetic and natural products for AIDS-antiviral activity. J. Natl. Cancer Inst. 81:577-586, 1989.

The Procedure is as follows:

1. The Candidate agent is dissolved in dimethyl sulfoxide (unless otherwise instructed) then diluted 1:100 in cell culture medium before preparing serial half-log$_{10}$ dilutions. T4 lymphocytes (CEM cell line) are added and after a brief interval HIV-1 added, resulting in a 1:200 final dilution of the compound. Uninfected cells with the compound serve as a toxicity control, and infected and uninfected cells without compound serve as basic controls.

2. Cultures are incubated at 37° in a 5% carbon dioxide atmosphere for 6 days.

3. The tetrazolium salt, XTT, is added to all wells, and cultures are incubated to allow formazan color development by viable cells.

4. Individual wells are analyzed spectrophotometrically to quantitate formazan production, and in addition are viewed microscopically for detection of viable cells and confirmation of protective activity.

5. Drug-treated virus-infected cells are compared with drug-treated noninfected cells and with other appropriate controls (untreated infected and untreated noninfected: cells, drug-containing wells without cells, etc.) on the same plate.

6. Data are reviewed in comparison with other tests done at the same time and a determination about activity is made.

The results on representative compounds are given hereinbelow:

IN-VITRO TESTING RESULTS - COMPOUND 1
CELL LINE: CEM-V

| Summary | | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | $>1.78 \times 10^{-4}$ | $5.68 \times 10^{-8}$ | 10.1 | $5.68 \times 10^{-8}$ | 120.4 |
| EC50 (Molar) | $8.08 \times 10^{-6}$ | $1.79 \times 10^{-7}$ | 10.3 | $1.79 \times 10^{-7}$ | 122.7 |
| TI50 (IC/EC) | $>2.20 \times 10^{+2}$ | $5.67 \times 10^{-7}$ | 10.6 | $5.67 \times 10^{-7}$ | 112.5 |
| Conclusion | | $1.79 \times 10^{-6}$ | 8.0 | $1.79 \times 10^{-6}$ | 120.9 |
| ACTIVE | | $5.66 \times 10^{-6}$ | 31.1 | $5.66 \times 10^{-6}$ | 118.8 |
| | | $1.79 \times 10^{-5}$ | 92.2 | $1.79 \times 10^{-5}$ | 117.9 |
| | | $5.65 \times 10^{-5}$ | 97.1 | $5.65 \times 10^{-5}$ | 121.2 |
| | | $1.78 \times 10^{-4}$ | 105.2 | $1.78 \times 10^{-4}$ | 122.9 |

IN-VITRO TESTING RESULTS - COMPOUND 1
CELL LINE: CEM-Z

| Summary | | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | $>1.78 \times 10^{-4}$ | $5.68 \times 10^{-8}$ | 56.5 | $5.68 \times 10^{-8}$ | 101.0 |
| EC50 (Molar) | $2.02 \times 10^{-6}$ | $1.79 \times 10^{-7}$ | 40.5 | $1.79 \times 10^{-7}$ | 100.6 |
| TI50 (IC/EC) | $>8.82 \times 10^{+2}$ | $5.67 \times 10^{-7}$ | 47.9 | $5.67 \times 10^{-7}$ | 99.6 |
| Conclusion | | $1.79 \times 10^{-6}$ | 47.1 | $1.79 \times 10^{-6}$ | 97.9 |
| ACTIVE | | $5.66 \times 10^{-6}$ | 74.5 | $5.66 \times 10^{-6}$ | 98.7 |
| | | $1.79 \times 10^{-5}$ | 85.7 | $1.79 \times 10^{-5}$ | 101.1 |
| | | $5.65 \times 10^{-5}$ | 92.3 | $5.65 \times 10^{-5}$ | 103.4 |
| | | $1.78 \times 10^{-4}$ | 90.9 | $1.78 \times 10^{-4}$ | 101.1 |

IN-VITRO TESTING RESULTS - COMPOUND 1
CELL LINE: CEM-V

| Summary | | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | $9.31 \times 10^{-7}$ | $5.68 \times 10^{-8}$ | 9.4 | $5.68 \times 10^{-8}$ | 99.0 |
| EC50 (Molar) | $1.44 \times 10^{-5}$ | $1.79 \times 10^{-7}$ | 8.7 | $1.79 \times 10^{-7}$ | 106.5 |
| TI50 (IC/EC) | $6.44 \times 10^{+2}$ | $5.67 \times 10^{-7}$ | 8.3 | $5.67 \times 10^{-7}$ | 77.9 |
| Conclusion | | $1.79 \times 10^{-6}$ | 9.3 | $1.79 \times 10^{-6}$ | 13.2 |
| ACTIVE | | $5.66 \times 10^{-6}$ | 36.6 | $5.66 \times 10^{-6}$ | 15.1 |
| | | $1.79 \times 10^{-6}$ | 53.1 | $1.79 \times 10^{-5}$ | 14.6 |
| | | $5.65 \times 10^{-5}$ | 29.0 | $5.65 \times 10^{-5}$ | 25.1 |
| | | $1.78 \times 10^{-4}$ | 6.4 | $1.78 \times 10^{-4}$ | 32.4 |

IN-VITRO TESTING RESULTS - COMPOUND 1
CELL LINE: CEM-Z

| Summary | | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | $>1.78 \times 10^{-4}$ | $5.68 \times 10^{-8}$ | 18.2 | $5.68 \times 10^{-8}$ | 104.3 |
| EC50 (Molar) | $4.19 \times 10^{-6}$ | $1.79 \times 10^{-7}$ | 16.8 | $1.79 \times 10^{-7}$ | 102.5 |
| TI50 (IC/EC) | $>4.25 \times 10^{+2}$ | $5.67 \times 10^{-7}$ | 23.3 | $5.67 \times 10^{-7}$ | 99.8 |
| Conclusion | | $1.79 \times 10^{-6}$ | 26.4 | $1.79 \times 10^{-6}$ | 99.7 |
| ACTIVE | | $5.66 \times 10^{-6}$ | 58.3 | $5.66 \times 10^{-6}$ | 100.0 |
| | | $1.79 \times 10^{-6}$ | 91.3 | $1.79 \times 10^{-5}$ | 103.0 |
| | | $5.65 \times 10^{-5}$ | 93.1 | $5.65 \times 10^{-5}$ | 101.8 |
| | | $1.78 \times 10^{-4}$ | 43.3 | $1.78 \times 10^{-4}$ | 72.1 |

IN-VITRO TESTING RESULTS - COMPOUND 1
CELL LINE: CEM-V

| | Summary | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | >1.89 × 10$^{-4}$ | 6.01 × 10$^{-8}$ | 14.7 | 6.01 × 10$^{-8}$ | 105.0 |
| EC50 (Molar) | 4.12 × 10$^{-6}$ | 1.90 × 10$^{-7}$ | 14.0 | 1.90 × 10$^{-7}$ | 96.9 |
| TI50 (IC/EC) | >4.58 × 10$^{+2}$ | 6.00 × 10$^{-7}$ | 15.5 | 6.00 × 10$^{-7}$ | 90.4 |
| Conclusion | | 1.89 × 10$^{-6}$ | 18.2 | 1.89 × 10$^{-6}$ | 97.9 |
| ACTIVE | | 5.99 × 10$^{-6}$ | 65.3 | 5.99 × 10$^{-6}$ | 111.2 |
| | | 1.89 × 10$^{-5}$ | 100.0 | 1.89 × 10$^{-5}$ | 99.9 |
| | | 5.98 × 10$^{-5}$ | 79.7 | 5.98 × 10$^{-5}$ | 104.7 |
| | | 1.89 × 10$^{-4}$ | 86.0 | 1.89 × 10$^{-4}$ | 86.7 |

IN-VITRO TESTING RESULTS - COMPOUND 1
CELL LINE: CEM-V

| | Summary | INFECTED CULTURE | | UNINFECTED CULTURE | |
|---|---|---|---|---|---|
| Index | Concentration | Dose(Molar) | Response (%) | Dose(Molar) | Response(%) |
| IC50 (Molar) | >1.89 × 10$^{-4}$ | 6.01 × 10$^{-8}$ | 8.7 | 6.01 × 10$^{-8}$ | 101.6 |
| EC50 (Molar) | 3.31 × 10$^{-6}$ | 1.90 × 10$^{-7}$ | 12.1 | 1.90 × 10$^{-7}$ | 105.1 |
| TI50 (IC/EC) | >5.70 × 10$^{+2}$ | 6.00 × 10$^{-7}$ | 8.3 | 6.00 × 10$^{-7}$ | 98.3 |
| Conclusion | | 1.89 × 10$^{-6}$ | 11.4 | 1.89 × 10$^{-6}$ | 104.6 |
| ACTIVE | | 5.99 × 10$^{-6}$ | 90.9 | 5.99 × 10$^{-6}$ | 111.3 |
| | | 1.89 × 10$^{-5}$ | 110.5 | 1.89 × 10$^{-5}$ | 100.7 |
| | | 5.98 × 10$^{-5}$ | 95.2 | 5.98 × 10$^{-5}$ | 99.2 |
| | | 1.89 × 10$^{-4}$ | 87.3 | 1.89 × 10$^{-4}$ | 89.8 |

In-Vitro Testing Results - COMPOUND 6
Cell Line: CEM-IW

| | SUMMARY | DOSE | INFECTED RESPONSE | UNINFECTED RESPONSE |
|---|---|---|---|---|
| Index | Concentration | (Molar) | Percent of Control | Percent of Control |
| IC50 (Molar) | >1.45 × 10$^{-4}$ | 4.60 × 10$^{-8}$ | 20.32 | 88.77 |
| EC50 (Molar) | 7.06 × 10$^{-7}$ | 1.45 × 10$^{-7}$ | 22.07 | 80.72 |
| TI50 (IC/EC) | >2.05 × 10$^{+2}$ | 4.60 × 10$^{-7}$ | 42.03 | 74.84 |
| Conclusion | | 1.45 × 10$^{-6}$ | 86.23 | 87.10 |
| ACTIVE | | 4.59 × 10$^{-6}$ | 94.00 | 90.01 |
| | | 1.45 × 10$^{-5}$ | 100.31 | 92.55 |
| | | 4.58 × 10$^{-5}$ | 99.01 | 100.68 |
| | | 1.45 × 10$^{-4}$ | 97.41 | 109.82 |

In-Vitro Testing Results - COMPOUND 6
Cell Line: CEM-IW

| | SUMMARY | DOSE | INFECTED RESPONSE | UNINFECTED RESPONSE |
|---|---|---|---|---|
| Index | Concentration | (Molar) | Percent of Control | Percent of Control |
| IC50 (Molar) | >1.45 × 10$^{-4}$ | 4.60 × 10$^{-8}$ | 13.88 | 104.88 |
| EC50 (Molar) | 8.29 × 10$^{-7}$ | 1.45 × 10$^{-7}$ | 17.90 | 98.46 |
| TI50 (IC/EC) | >1.75 × 10$^{+2}$ | 4.60 × 10$^{-7}$ | 29.70 | 97.86 |
| Conclusion | | 1.45 × 10$^{-6}$ | 82.50 | 93.92 |
| ACTIVE | | 4.59 × 10$^{-6}$ | 92.81 | 96.62 |
| | | 1.45 × 10$^{-5}$ | 95.03 | 97.21 |
| | | 4.58 × 10$^{-5}$ | 95.59 | 106.72 |
| | | 1.45 × 10$^{-4}$ | 94.22 | 97.75 |

| In-Vitro Testing Results - COMPOUND 6 Cell Line: CEM-IW | | | | |
|---|---|---|---|---|
| SUMMARY | | DOSE | INFECTED RESPONSE | UNINFECTED RESPONSE |
| Index | Concentration | (Molar) | Percent of Control | Percent of Control |
| IC50 (Molar) | >1.45 × 10$^{-4}$ | 4.60 × 10$^{-8}$ | 9.51 | 105.92 |
| EC50 (Molar) | 1.14 × 10$^{-6}$ | 1.45 × 10$^{-7}$ | 9.36 | 109.08 |
| TI50 (IC/EC) | >1.27 × 10$^{+2}$ | 4.60 × 10$^{-7}$ | 24.44 | 88.80 |
| Conclusion | | 1.45 × 10$^{-6}$ | 62.75 | 100.12 |
| ACTIVE | | 4.59 × 10$^{-6}$ | 84.87 | 82.26 |
| | | 1.45 × 10$^{-5}$ | 82.49 | 84.55 |
| | | 4.58 × 10$^{-5}$ | 83.75 | 80.53 |
| | | 1.45 × 10$^{-4}$ | 83.35 | 89.72 |

| In-Vitro Testing Results - COMPOUND 6 Cell Line: CEM-IW | | | | |
|---|---|---|---|---|
| SUMMARY | | DOSE | INFECTED RESPONSE | UNINFECTED RESPONSE |
| Index | Concentration | (Molar) | Percent of Control | Percent of Control |
| IC50 (Molar) | >1.45 × 10$^{-4}$ | 4.60 × 10$^{-8}$ | 11.28 | 111.46 |
| EC50 (Molar) | 8.92 × 10$^{-7}$ | 1.45 × 10$^{-7}$ | 14.32 | 105.53 |
| TI50 (IC/EC) | >1.62 × 10$^{+2}$ | 4.60 × 10$^{-7}$ | 37.65 | 107.87 |
| Conclusion | | 1.45 × 10$^{-6}$ | 68.40 | 105.53 |
| ACTIVE | | 4.59 × 10$^{-6}$ | 80.73 | 98.81 |
| | | 1.45 × 10$^{-5}$ | 79.91 | 104.22 |
| | | 4.58 × 10$^{-5}$ | 82.81 | 105.99 |
| | | 1.45 × 10$^{-4}$ | 80.76 | 104.62 |

Additional results are summarized hereinbelow.

| $R_1$ | $R_2$ | $T_1$ | $T_2$ | X | CEM-IW $EC_{50}$, M | MT-2 $EC_{50}$, M |
|---|---|---|---|---|---|---|
| NO2 | H | H | H | SO2 | 4.41E-06 | 1.16E-06 |
| H | H | H | H | SO2 | — | 7.75E-05 |
| NO2 | H | H | Me | SO2 | 1.45E-05 | 3.26E-06 |
| NO2 | H | H | Cl | SO2 | 4.29E-05 | 3.82E-05 |
| NO2 | H | NO2 | H | S | 7.87E-06 | 5.77E-06 |
| H | H | H | H | SO | — | 3.58E-04 |
| NO2 | H | NO2 | H | SO2 | 5.44E-06 | 7.47E-07 |
| (N)* | H | H | H | SO2 | 2.06E-04 | 7.57E-05 |

*Pyridine ring with the N at position $R_1$.

Obviously, there is a structure activity relationship with respect to the efficacy of the compounds of the present invention. Factors that affect the relationship may include steric effects, electronic effects, (electron withdrawing or electron donating ability), resonance effects, hydrophobic, hydrophilic, hydrogen bonding parameters, etc. The data in the tables suggest certain trends: (a) An o-nitro group on diphenyl sulfone increases anti-HIV activity, (b) A p-nitro group on diphenyl sulfone increases cytotoxicity and appears to render the compound undesirable as a chemotherapeutic agent, (c) An amino group ortho or para on diphenyl sulfone administer anti-HIV activity. Thus, these trends suggest a relationship between the structure of the compound and its activity or $EC_{50}$, i.e. the concentration of active compound to reduce the retroviral concentration by 50%. Based on the data, it has been determined that there is a direct correlation between the log $(EC_{50})^{-1}$ and the electronic effect of a substituent (a) or more precisely the sum of the sigma ($\sigma$) values. (The greater the electron withdrawing ability of a substituent, the higher the value of $\sigma$, while a better electron donating group has a lower value of $\sigma$.) There appears to be a direct correlation between log $(EC_{50})^{-1}$ and the $\Sigma\sigma$; as the $\Sigma\sigma$ increases, so does the log $(EC_{50})^{-1}$. The addition of substituents to the diphenyl sulfone will affect the factors discussed hereinabove, thus both the log $(EC_{50})^{-1}$ and the $\Sigma\sigma$ will be affected. Thus for the diphenyl sulfone derivative

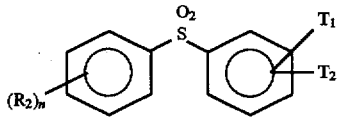

the relation is $$(\log EC_{50})^{-1} = 1.039\Sigma\sigma + 4.415 \quad EQ1$$

This relationship is a linear correlation between $\Sigma\sigma$ and (log $EC_{50})^{-1}$. (See FIG. 1). Furthermore, this relationship quantities anti-HIV activity with sigma values and hence with electrons donating or withdrawing power of various groups, the latter type of group enhancing anti-HIV activity. The $\sigma$ values may range from −4.00 to +4.00. It is preferred that the $\sigma$ values range from −1.00 to 4.00.

Two developmental suggestions follow from the relationship. One is that the anti-HIV activity of 2-nitrodiphenyl sulfone may be augmented by the introduction of additional electron-withdrawing groups. In part, this suggestion is strengthened by the increased potency of 2,2'-dinitrodiphenyl sulfone.

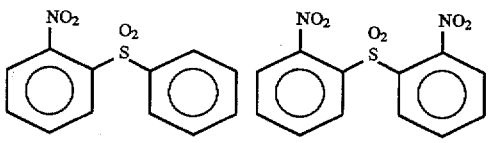

Another developmental suggestion is that, in 2-nitrodiphenyl sulfone, the nitro group itself might be replaced by different electron-withdrawing groups with the result that the modified compound may yet show anti-HIV activity. In 2-nitrodiphenyl sulfone, for example, the nitro group may be replaceable by CN, NO, and other groups with large positive $\sigma_o$ values. Although few reliable values for $\sigma_o$ are available, it has been noted that the $\sigma_o$ values are approximated by up values, and suitable replacement candidates may be chosen on the latter basis. Encouragement is afforded by aza situation wherein the o-nitrophenyl unit is replaced by the 2-pyridyl unit: phenyl 2-pyridyl sulfone shows anti-HIV activity.

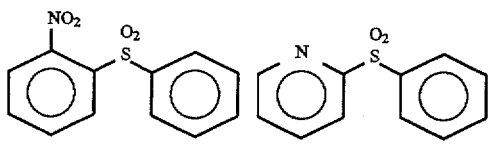

The compounds of the correlation can be subdivided into two intersecting subsets. The first of these subsets includes diphenyl sulfone and its 2-amino-, 2-nitro-, 2,2'-dinitro-derivatives. There the potencies span two powers of the ten in the correlation $$\log(EC_{50})^{-1} = 1.070\Sigma\sigma + 4.419 \ (n=4; \ r=0.994)$$

Figure 2:
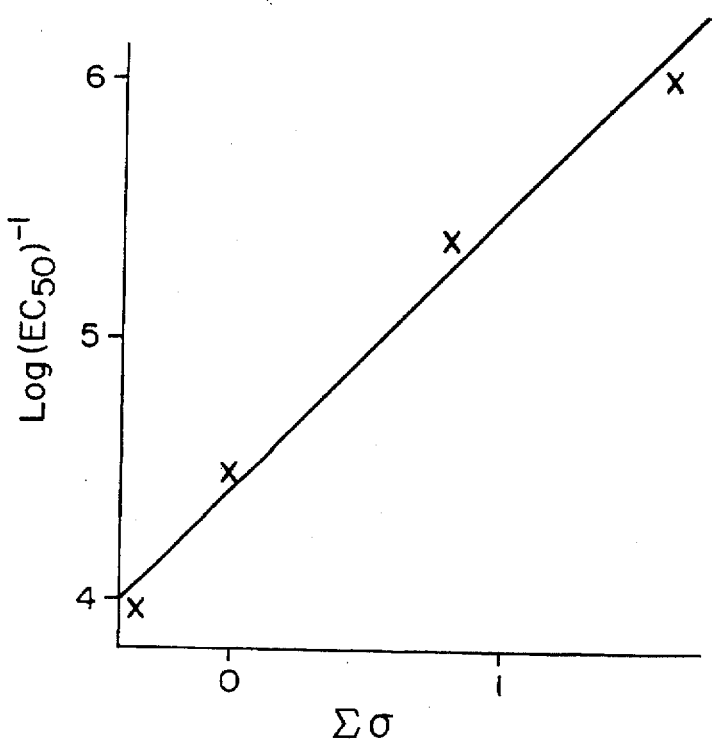
FIG. 2 is a plot of log $(EC_{50})^{-1}$ and $\sigma$ for a subset of diaryl sulfones.

Although the attached groups are structurally very restricted, they embrace extremes from a strong electron-donor (NH₂) to a strong electron-withdrawing group (NO₂). (See FIG. 2).

The 4'-substituted-2-nitrodiphenyl sulfones constitute the second subset. Their data points account for much of the scatter in the larger linear relationship. The 4'-substituents (Cl, H, Me, MeO) vary from a mildly electron-withdrawing group to a strongly electron-releasing group. Although log $(EC_{50})^{-1}$ for those points over their very limited range do not correlate well with either $\sigma$ or $\sigma-(r<0.7)$, they correlate somewhat better with $\sigma^+$;

$$\log(EC_{50})^{-1} = 0.558\sigma^+ + 5.346 \ (n=4; \ r=0.919).$$

Figure 3:
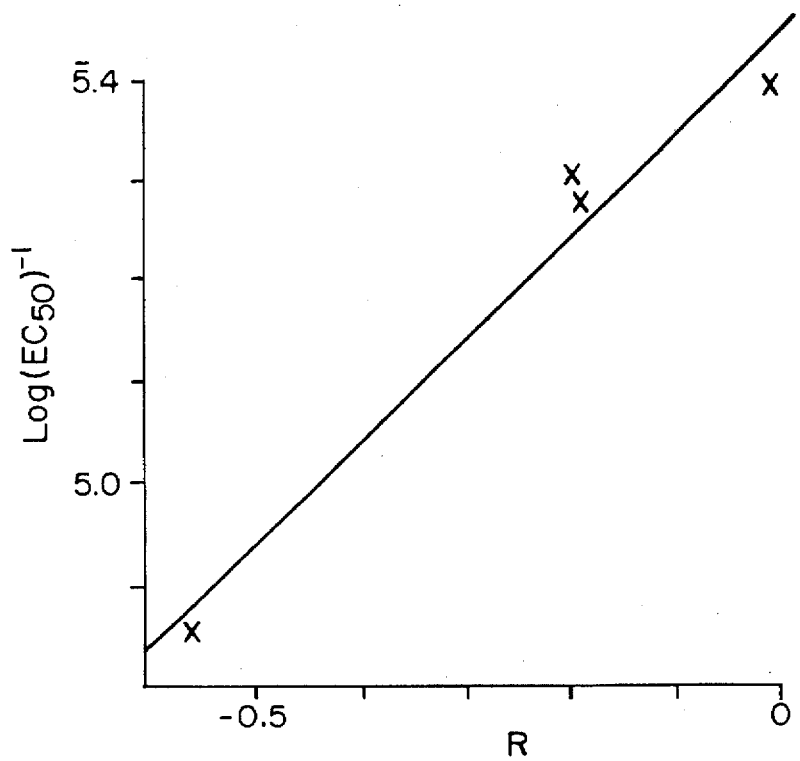
FIG. 3 is a plot of log $(EC_{50})^{-1}$ and R for 2-nitrodiphenylsulfones and its 4-substituted derivatives.

Better still is a correlation with $R^1$, the resonance component of the substituents' $\sigma$ a value (FIG. 3).

$$\log(EC_{50})^{-1} = 1.018R^1 + 5.445 \ (n=4; \ r=0.984)$$

The developmental suggestion here is that greater potency may be achieved by adding onto the 2-nitrodiphenyl sulfone skeleton groups with large positive R-values.

Two sulfoxides and two sulfonate esters also show moderate activity in

Figure 4:
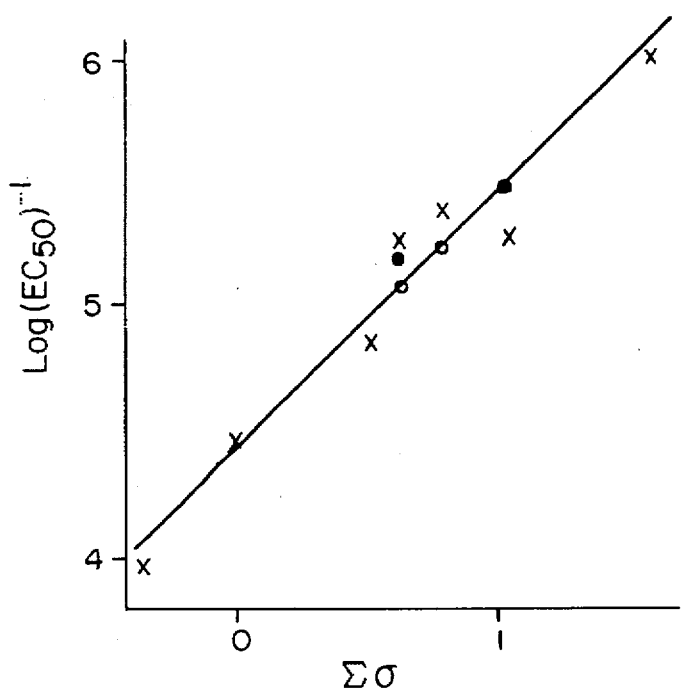
FIG. 4 is a plot of log $(EC_{50})^{-1}$ and $\sigma$ for sulfonyl(x), sulfoxides(o) and sulfonate esters(●).

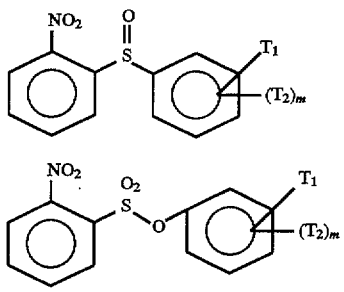

anti-HIV assays. Interestingly, if the points for their respective values for $\log(EC_{50})^{-1}$ and $\Sigma\sigma$ for their aromatic ring substituents are plotted on the same graph with the sulfones, they fall very close to the correlation line (FIG. 4). When the results are included in the sulfone correlation, a new correlation emerges which is nearly identical with the correlation for the sulfones alone:

$$\log(EC_{50})^{-1} = 1.043\Sigma\sigma + 4.433 \ (n=11; \ r=0.977)$$

The implication of this extended correlation is that the unit linking the aromatic rings is open to some variability; the —SO₂—, —SO—, and —SO₂O— bridges appear to be equivalent. However, the bridging unit has structural limitations. Two moderately active sulfides (with the —S— bridge) provide

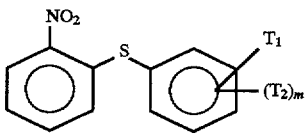

points which do not appear to be collinear with the correlation line.

Thus, while the invention has been described with reference to certain preferred embodiments, those skilled in the art will realize that changes and modifications may be made thereto without departing from the full and intended scope of the appended claims.

What is claimed:

1. A method of treating a retrovirus infection in an animal which comprises administering to the animal a therapeutically effective amount of a compound represented by the following structural formula:

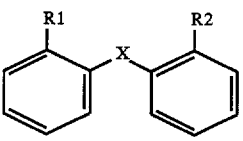

or pharmaceutically acceptable salts thereof, wherein:

X is selected from the group consisting of —S—, —SO—, —SO₂— and —SO₂O—; and

R1 and R2 are each independently selected from the group consisting of —H and —NO$_2$, with the proviso that R1 and R2 are not both —H.

2. The method of claim 1 wherein X is —SO$_2$.

3. The method of claim 2 wherein R1 and R2 are each —NO$_2$.

4. The method of claim 2 wherein R1 is —H.

5. A method of treating a retrovirus infection in an animal which comprises administering to the animal a therapeutically effective amount of a compound represented by the following structural formula:

Ar—X—Ar' or pharmaceutically acceptable salts thereof, wherein:

X is selected from the group consisting of —S—, —SO—, —SO$_2$— and —SO$_2$O—; and Ar is 2-pyridyl and and Ar' is 2-(R5)-phenyl, wherein R5 is H or —NO$_2$.

6. The method of claim 5 wherein the compound is represented by the following structural formula:

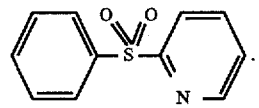

* * * * *